(12) United States Patent
Arthun

(10) Patent No.: US 6,779,575 B1
(45) Date of Patent: Aug. 24, 2004

(54) SEALING APPLIANCE

(75) Inventor: Nils Arthun, Ockero (SE)

(73) Assignee: Novaseptum AB (SE)

( * ) Notice: Subject to any disclaimer, the term of this patent is extended or adjusted under 35 U.S.C. 154(b) by 0 days.

(21) Appl. No.: 09/701,459

(22) PCT Filed: May 25, 1999

(86) PCT No.: PCT/SE99/00878
§ 371 (c)(1),
(2), (4) Date: Dec. 4, 2000

(87) PCT Pub. No.: WO99/64837
PCT Pub. Date: Dec. 16, 1999

(30) Foreign Application Priority Data

May 28, 1998 (SE) ............................................. 9801885

(51) Int. Cl.[7] .............................................. B32B 31/18
(52) U.S. Cl. ..................... 156/515; 156/530; 156/579; 156/581; 72/409.19
(58) Field of Search ................................ 156/519, 515, 156/530, 580, 581; 100/94, 98 R; 72/702, 307, 370.12, 409.19, 409.05, 409.1, 325, 461

(56) References Cited

U.S. PATENT DOCUMENTS

| 4,637,242 A | * | 1/1987 | Undin et al. | ................... | 72/410 |
| 5,732,530 A | * | 3/1998 | Pfaff | ............................ | 53/403 |
| 5,768,935 A | * | 6/1998 | Owens | ......................... | 72/416 |
| 5,775,158 A | * | 7/1998 | Hensley et al. | ................ | 30/180 |

FOREIGN PATENT DOCUMENTS

| EP | 0508474 | 10/1992 | ........... B29C/65/20 |
| WO | 9716715 | 5/1997 | ............ G01N/1/10 |

* cited by examiner

Primary Examiner—Richard Crispino
Assistant Examiner—George R. Koch, III
(74) Attorney, Agent, or Firm—Orum & Roth

(57) ABSTRACT

An appliance for sealing elastic hoses with a sleeve, which is plastically deformable and slipped onto the hose, has two jaws which are movable towards and away from each other. One jaw has two straight bars which project towards the other jaw and extend transversely of the sleeve to make two transverse indentations in the sleeve and the hose when the jaws are moving towards each other. The same jaw has a cutting edge which projects towards the other jaw and is directed transversely of the sleeve, the cutting edge making a substantially transverse cutting indication in the sleeve and the hose when the jaws are moving towards each other.

18 Claims, 5 Drawing Sheets

SEALING APPLIANCE

TECHNICAL FIELD

The present invention relates to an appliance for mechanical sealing of hollow hoses of elastic material with a sealing means which is made of plastically deformable material and which is applied to the hose, said appliance having two jaws, which are movable towards and away from each other and which, when moving towards each other, crimp the sealing means against the hose to seal the same.

BACKGROUND OF THE INVENTION

In a prior-art sealing appliance of the type mentioned by way of introduction, the sealing means in the form of a folded clip is applied to a likewise folded end of the hose. The clip is then crimped against the hose to seal the same, after which the hose is cut downstream of the clip by means of a pair of scissors or some other cutting tool.

As the relevant hoses have a relatively small diameter, say 5–10 mm, the clips are also relatively small and often difficult to apply in the right position on the folded end of the hose. Nor is it infrequent that the clip falls off the end of the hose, before the sealing appliance has managed to grip it for crimping against the hose with the ensuing risk of sealing not taking place.

The sealing appliance according to the invention is primarily to be used in the type of device which is intended for introduction and/or withdrawal of a medium in a container and which is disclosed and described in WO 97/16715. More specifically, it is intended for contamination-free sealing and cutting of the hoses which extend between the conveying means and the collecting vessels which are connected to the process container, so that the collecting vessels after being filled with a medium from the process container can be moved without any risk of contamination to a laboratory or the like for sampling or analysis of the medium.

In the above use of the sealing appliance, which requires good hygienic conditions and contamination-free environment/surroundings, clips of the mentioned type are unacceptable. One reason for this is that they are difficult to handle and often do not provide the desired sealing. Another reason is that there is in most cases at least a small portion of the hose left downstream of the clip containing a small quantity of the medium which leaks out to the surrounding area with an obvious risk of contamination.

OBJECT OF THE INVENTION

The main object of the present invention is to provide a sealing appliance of the type mentioned by way of introduction, satisfying all the requirements for contamination-free transport of the relevant collecting vessels, which are filled with a medium, to the laboratory or the like.

SUMMARY OF THE INVENTION

This as well as related objects are achieved in a simple and efficient manner in that the sealing means has the form of a sleeve which is slipped on to the hose, that at least one of the jaws has at least one bar which projects towards the other jaw and which, when the jaws are moving towards each other, makes an indentation in the sleeve and the hose to reinforce the sealing thereof as well as the fixing of the sleeve on the hose, and that at least one of the jaws has a cutting means, which projects towards the other jaw and which, when the jaws are moving towards each other, makes a cutting indication in the sleeve and the hose to allow a sealing cutting of the hose.

In a particularly preferred embodiment there are at least two straight bars which are arranged substantially in parallel at a distance from each other and extend substantially transversely of the longitudinal direction of the sleeve to make a corresponding number of substantially transverse indentations in the sleeve and the hose, the cutting means preferably extending substantially transversely of the longitudinal direction of the sleeve and making a substantially transverse cutting indication in the sleeve and the hose.

BRIEF DESCRIPTION OF THE DRAWINGS

The invention will be described below in more detail with reference to the accompanying drawings, in which.

DESCRIPTION OF A PREFERRED EMBODIMENT

Figure 1:
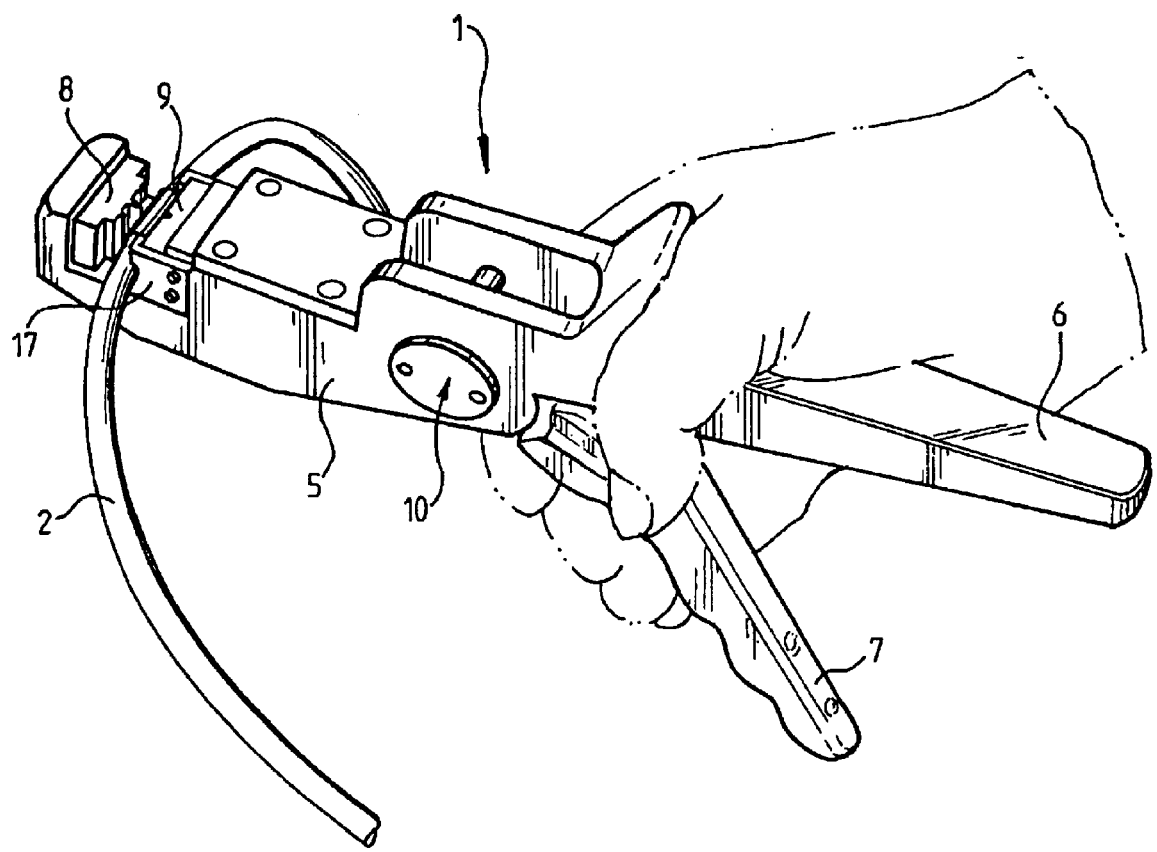
FIG. 1 is a perspective view, seen obliquely from above, of an appliance according to a currently particularly preferred embodiment of the invention in an initial position for the sealing of a hose.

As mentioned above, the appliance generally designated 1 is primarily conceived for use in the type of device which is intended for introduction and/or withdrawal of a medium in a container and which is disclosed and described in WO 97/16715. More specifically, it is intended for sealing and cutting the hoses in a mechanical and contamination-free manner, which extend between the conveying means and the collecting vessels which are connected to the process container, so that the collecting vessels after being filled with a medium from the process container can be transported without any risk of contamination to a laboratory or the like for sampling or analysis of the medium.

Still, the appliance 1 can, of course, also be used in a number of other applications where good hygienic conditions and/or contamination-free surroundings and/or working environment are required to a varying extent.

Thus the appliance 1 is generally intended for mechanical sealing of hollow hoses 2 of elastic material, e.g. rubber or plastic, of a quality which is suitable for the purpose. The sealing is carried out with the aid of a sealing means 3, which is made of a plastically deformable material, e.g. plastic or metal, having suitable plastic properties and which is applied to the hose 2. In the preferred embodiment shown, the sealing means 3 consists of a metal sleeve 4 which has been slipped on to the hose 2 in advance. The sleeve has a length of preferably two or more multiples of the diameter of the hose 2, which in turn is typically in the range of 5–10 mm.

Figure 3:
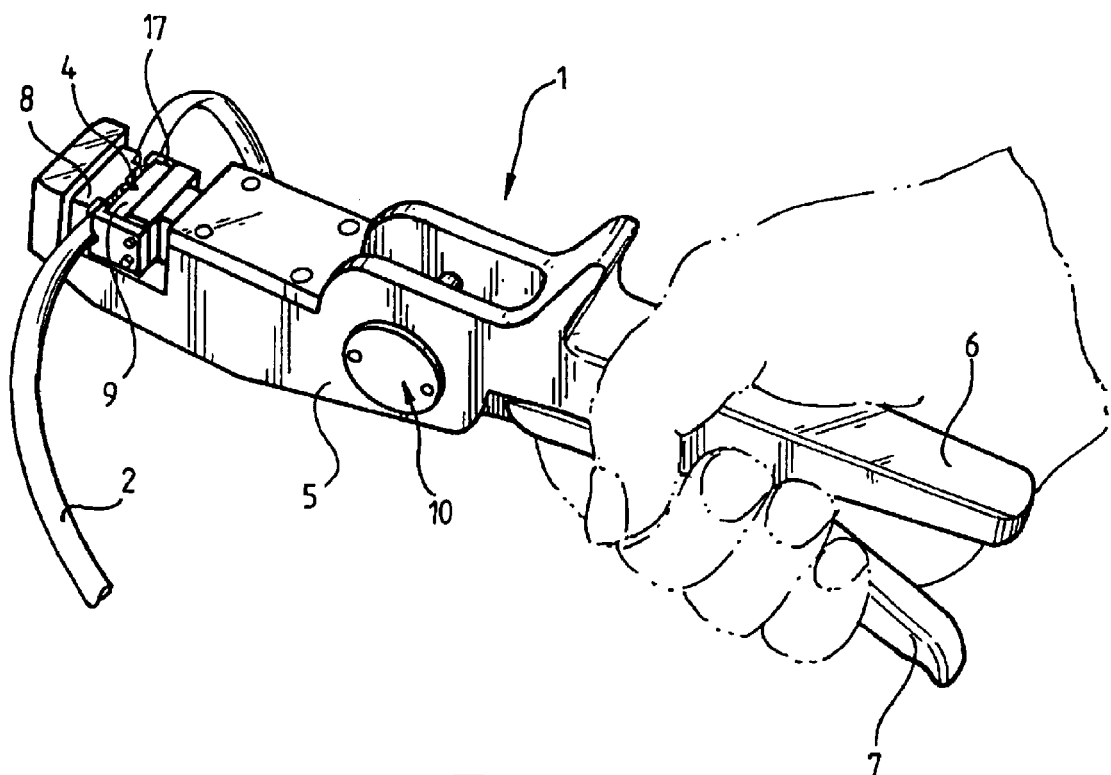
FIG. 3 is a perspective view of the appliance corresponding to FIG. 1 in end position of the sealing.

As shown in FIGS. 1 and 3, the appliance 1 itself can have the form of a pair of tongs 5 which is hand-operated and which has one fixed and one movable leg 6 and 7 and two jaws 8 and 9 which are movable towards and away from each other. When moving the jaws 8, 9 towards each other by manually pressing the legs 6, 7 together and using a driving means 10, which will be described below, the sleeve 4 is crimped against the hose 2, thereby sealing the same.

Figure 2:
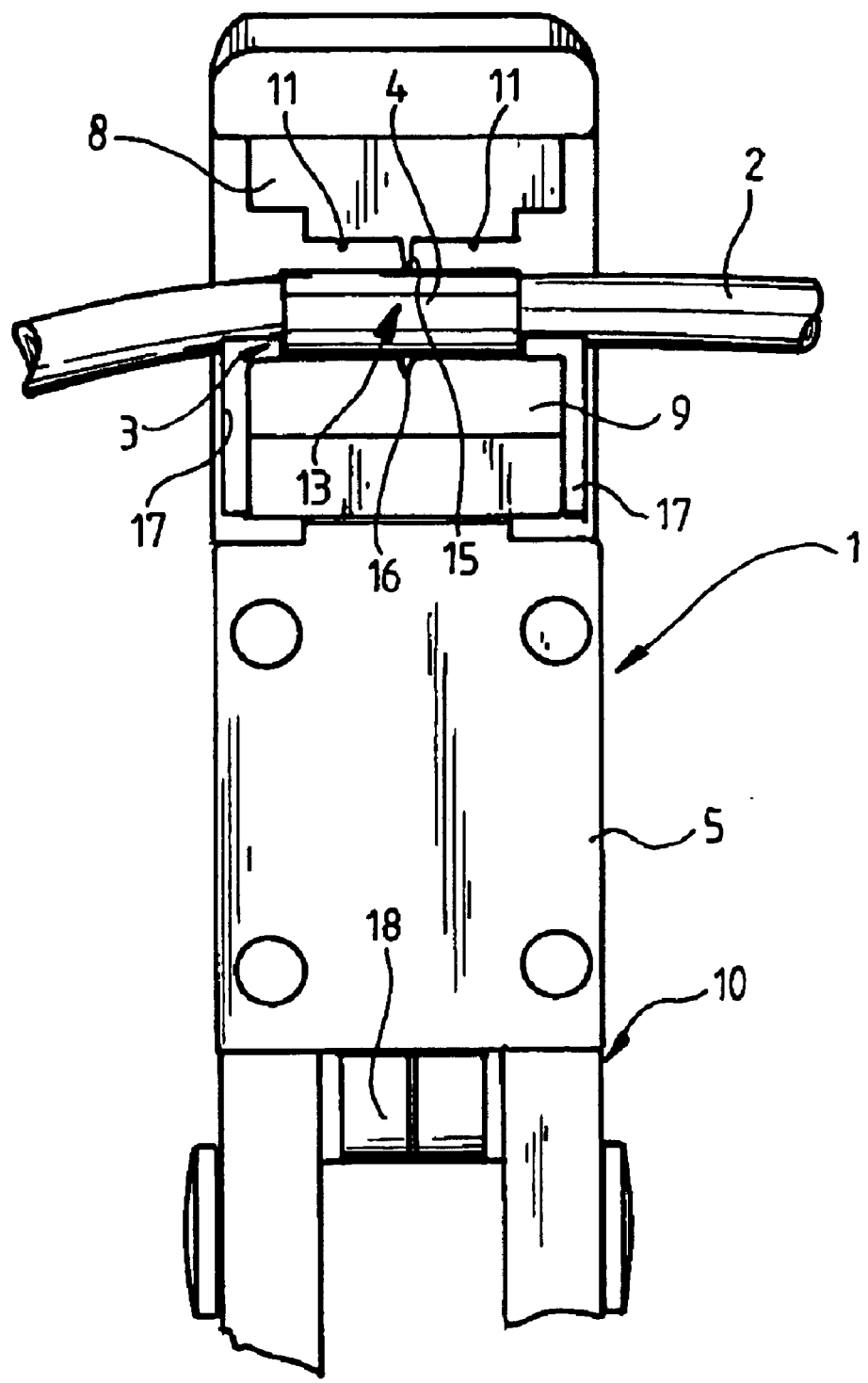
FIG. 2 is a front view of a part of the appliance according to FIG. 1 in the initial position.

More specifically, as best seen in FIG. 2, at least one of the jaws 8 or 9, in this case the jaw 8, has at least one bar 11 which projects towards the other jaw 9 or 8, in this case the jaw 9. In the above-described movement of the jaws 8, 9 towards each other, this bar 11 makes a marked indentation 12, se FIGS. 4, 5A and 5B, in the sleeve 4 and in the hose 2. In the preferred embodiment, there are two such bars 11, which are placed substantially in parallel at a distance from each other and extend substantially transversely of the longitudinal direction of the sleeve 4. The bars 11 are preferably straight and make two substantially transverse indentations 12 in the sleeve 4 and in the hose 2 to reinforce the sealing thereof as well as the fixing of the sleeve 4 on the hose 2. If desired and if suitable, there may, of course, be more than two such bars 11 or bars which are differently placed/formed on said jaw 8.

Figure 4:
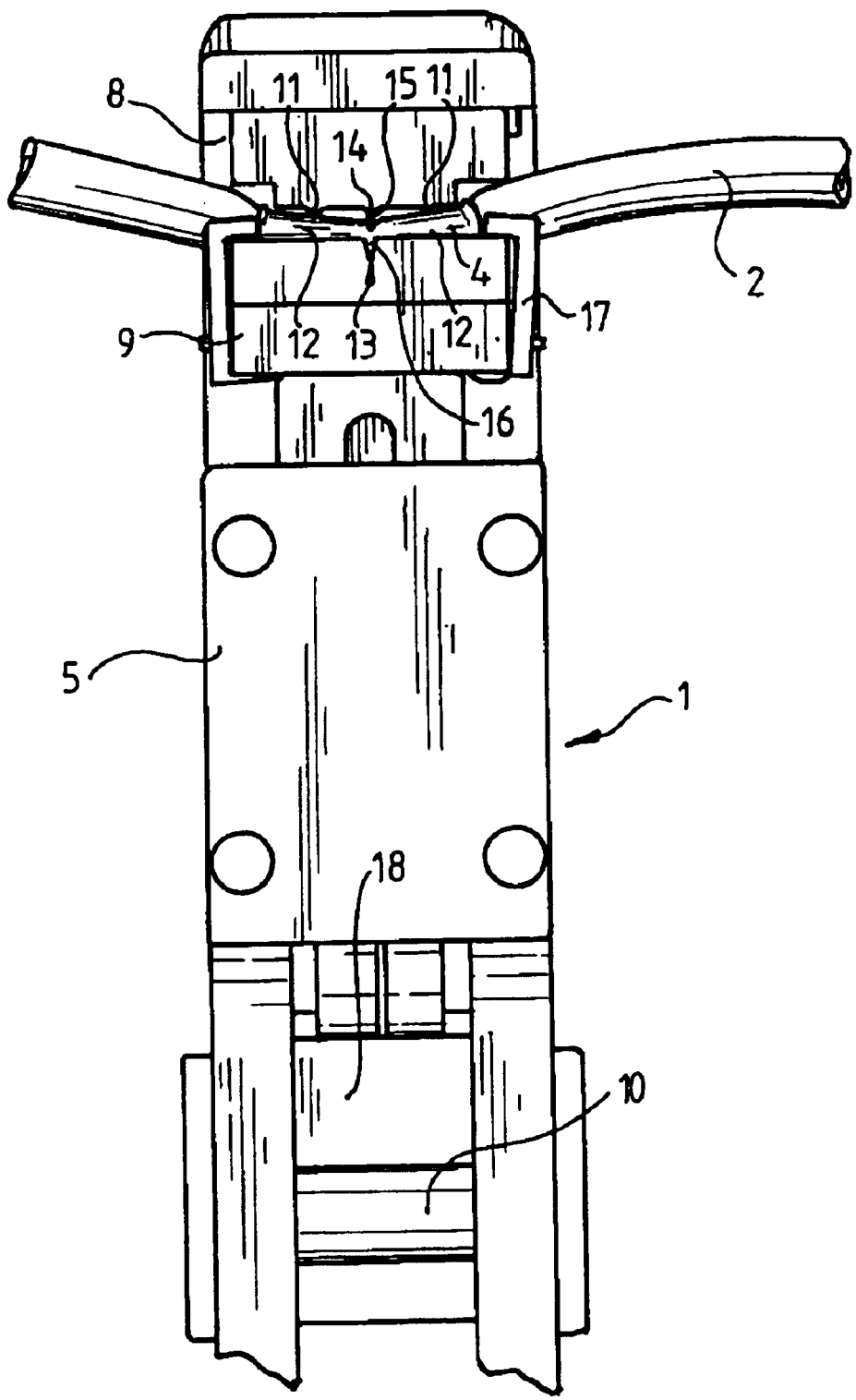
FIG. 4 is a view corresponding to FIG. 2, the appliance being in the end position.

Moreover, at least one of the jaws 8 or 9, also in this case the jaw 8, has a cutting means 13 projecting towards the other jaw 9 or 8 (see FIGS. 2 and 4). When the jaws 8, 9 are moving towards each other in the described manner, this cutting means 13 makes a cutting indication 14 in the sleeve 4 and in the hose 2 to allow the sleeve and the hose to be cut in a sealing manner.

In the shown embodiment, the cutting means 13 is preferably formed as a substantially straight cutting edge 15. The cutting edge extends substantially transversely of the longitudinal direction of the sleeve 4 and thus makes a substantially transverse cutting indication 14 in the sleeve 4 and in the hose 2. As seen in FIGS. 2 and 4, the cutting edge 15 projects to greater extent than the bars 11 and suitably co-operates with an opposite, straight recess 16 in the opposite jaw, in this case the jaw 9. The depth, width and form of the recess 16 can vary, and the recess is suitably adapted to the form of the cutting edge 15 and to the qualities of the material of the hose 2 and the sleeve 4. In certain applications, the recess 16 can, if required or desired, be omitted.

Preferably, the cutting edge 15 is situated substantially halfway between the bars 11, if they are two in number, such as shown in FIGS. 2 and 4. If there are further bars 11, the cutting edge 15 is suitably placed halfway between two adjacent bars, preferably the ones situated closest to the middle. In a certain application, it is, of course, also possible to place the cutting edge 15 outside or on one side of the bar or the bars 11.

Figure 5A:
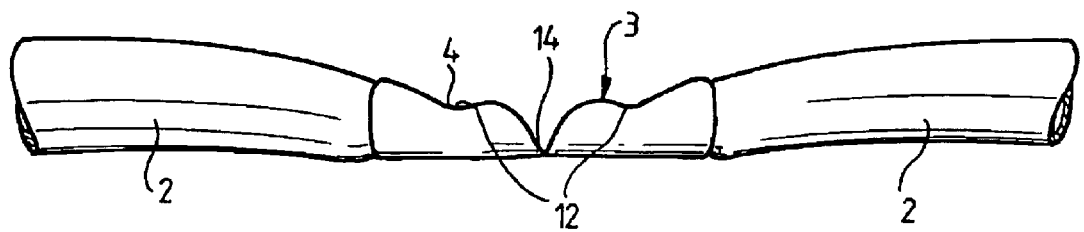
FIGS. 5A and 5B are side views which show the sealed hose, partially cut open, in a position after sealing and in a position after completed cutting of the hose.
Figure 5B:
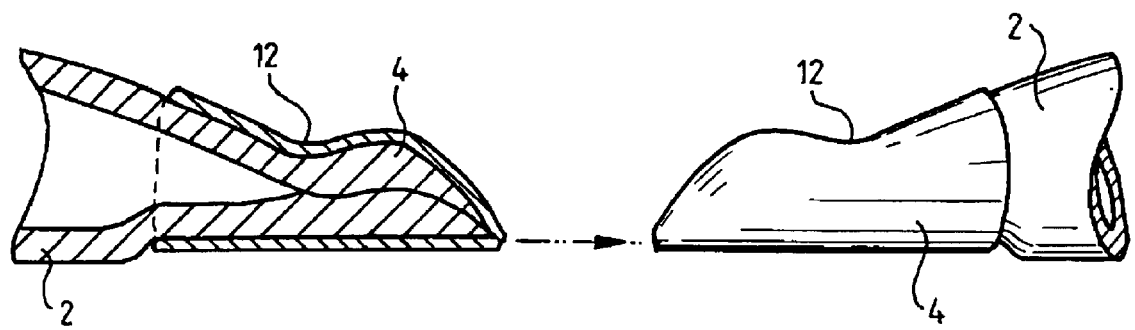

The cutting indication 14 mentioned above is preferably such that the sleeve 4 and the hose 2 are not cut or broken directly when sealing by means of the appliance 1, such as shown in FIG. 5A, but at an optional point of time after that. Then the sleeve 4 and the hose 2 are separated along the cutting indication 14 by manual or mechanical bending back and forth, until the sleeve is divided by fatigue fracture, as shown in FIG. 5B.

Naturally, nothing prevents the sleeve 4 and the hose 2 from being separated along the cutting indication 14 directly in connection with the actual sealing.

To fix the sleeve 4 and the hose 2 in the intended position between the jaws 8 and 9 in the appliance 1 when sealing, at least one of the jaws 8 or 9, in this case the jaw 9, has a fixture 17. The fixture fixes and supports the hose 2 and the sleeve 4 laterally, horizontally and vertically and can be formed in an optional manner which is not described in further detail.

For practical and other reasons, in the disclosed and described embodiment the bars 11 and the cutting edge 15 are arranged on one of the jaws 8 or 9, in this case the jaw 8, and the fixture 17 on the other, opposite jaw 9 or 8, in this case the jaw 9. The bars 11, the cutting edge 15 and the fixture 17 can be mounted on the associated jaw 8, 9 with the aid of suitable attachment means, which are not shown. Alternatively, one/some of or all these components can be made in one piece with the associated jaw. In the shown case, the bars 11 and the cutting edge 15 are made in one piece with the associated jaw, whereas the fixture 17 is mounted on the associated jaw, see FIGS. 2 and 4.

In the preferred embodiment, the jaw 8 provided with the bars 11 and the cutting edge 15 suitably has the form of a die which is fixedly mounted in the appliance 1 with the aid of attachment means (not shown), see FIGS. 2 and 4. In a corresponding manner, the jaw 9 provided with the fixture 17 has the form of a punch. This punch is mounted in a slidable manner (not shown) in the appliance 1 and is actuatable by the previously mentioned driving means 10. The driving means 10 suitably consists of a gear generally designated 18, which can be an eccentric mechanism or the like and which is suitably connected to and actuatable by means of the movable leg 7 of the pair of tongs 5.

The invention is not, of course, limited to the embodiment which is described above and shown in the drawings, and can be modified in many different ways within the scope of protection according to the appended claims.

The appliance 1 does not, for example, need to be a manually operable pair of tongs, but it can alternatively be a separate tool or a tool which is included in a machine and driven electrically, pneumatically, hydraulically etc according to need and desire. The jaws 8, 9 with the associated components (bars 11, cutting edge 15 and fixture 17) can be attached to the appliance 1 in a replaceable manner and match the size of the hose 2 and the sleeve 4 and/or be mutually exchangeable etc.

What is claimed is:

1. An appliance for mechanical sealing of hollow hoses (2) of elastic material with a sealing means (3) which is made of plastically deformable material and which is applied to the hose, said appliance (1) having two jaws (8, 9), at least one of the jaws is movable towards and away from the other jaw and the jaws crimp the sealing means (3) against the hose (2) to seal the same, characterised in that the sealing means (3) has the form of a sleeve (4) which is slipped on to the hose (2), that at least one of the jaws (8 or 9) has at least one straight bar (11) having a projecting end which projects towards the other jaw (9 or 8) and which, when at least one the jaws is moving towards the other jaw, makes an indentation (12) in the sleeve (4) and the hose (2) to reinforce the sealing thereof as well as the fixing of the sleeve on the hose, that at least one of the jaws (8 or 9) has a cutting means (13), which projects towards the other jaw (9 or 8) and which when at least one of the jaws (8, 9) is moving towards the other jaw, makes a cutting indication (14) in the sleeve (4) and the hose (2) to allow a sealing cutting of the hose (2), and that the cutting means (13) has the form of a substantially straight cutting edge (15) which projects to a greater extent than the projecting end of said at least one bar (11).

2. An appliance according to claim 1, characterized in that there are at least two straight bars (11) having projecting ends which are arranged substantially in parallel at a distance from each other and extend substantially transversely of the longitudinal direction of the sleeve (4) to make a corresponding number of substantially transverse indentations (12) in the sleeve (4) and the hose (2), and that the cutting means (13) extends substantially transversely of the longitudinal direction of the sleeve (4) and makes a substantially transverse cutting indication (14) in the sleeve (4) and the hose (2).

3. An appliance according to claim 2, characterized in that the cutting means (13) has the form of a substantially straight cutting edge (15), which projects to a greater extent than the projecting ends of the at least two straight bars (11).

4. An appliance according to claim 3, characterized in that
   the cutting edge (15) cooperates with an opposite recess (16) in the other jaw (9 or 8) and is situated substantially halfway between two adjacent bars (11);
   at least one of the jaws (8 or 9) has a fixture (17) to position the sleeve (4) and the hose (2) between the jaws (8, 9);
   the bars (11) and the cutting edge (15) are situated on one jaw (8) and that the fixture (17) is situated on the other jaw (9), the bars, the cutting edge and the fixture being mounted on or being make in one piece with the associated jaw,
   the jaw (8) provided with the bars (11) an the cutting edge (15) has the form of a die, which is fixedly mounted in the appliance (1) and the jaw (9) provided with the fixture (17) has the form of a punch, which is movably arranged in the appliance (1) and actuatable by a driving means (10); and
   the appliance has the form of a pair of tongs (5) which is hand operated and has one fixed and one movable leg (6, 7), the movable leg (7) actuating the jaw (9) forming the punch by means of a gear drive.

5. An appliance according to claim 3, characterized in that
   the cutting edge (15) cooperates with an opposite recess (16) in the other jaw (8 or 9);
   the cutting edge (15) is situated on one side of the bars (11);
   at least one of the jaws (8 or 9) has a fixture (17) to position the sleeve (4) and the hose (2) between the jaws (8, 9);
   the bars (11) and the cutting edge (15) are situated on one jaw (8) and the fixture (17) is situated on the other jaw (9), the bars, the cutting edge and the fixture being mounted on or being made in one piece with the associated jaw;
   the jaw (8) provided with the bars (11) and the cutting edge (15) has the form of a die, which is fixedly mounted in the appliance (1) and the jaw (9) provided with the fixture (17) has the form of a punch, which is movably arranged in the appliance (1) and actuatable by driving means (10); and
   the appliance has the form of a pair of tongs (5) which is hand operated and has one fixed and one movable leg (6, 7), the movable leg (7) actuating the jaw (9) forming the punch by means of a gear device.

6. An appliance according to claim 2, characterized in that at least one of the jaws (8 or 9) has a fixture (17) to position the sleeve (4) and the hose (2) between the jaws (8, 9).

7. An appliance according to claim 2, characterized in that the at least two bars (11) and the cutting edge (15) are situated on one jaw (8), and that the fixture (17) is situated on the other jaw (9), at the least one bar, the cutting edge and the fixture being mounted on or being make in one piece with the associated jaw.

8. An appliance according to claim 1, characterized in that the cutting edge (15) co-operates with an opposite recess (16) in the other jaw (9 or 8).

9. An appliance according to claim 8, characterized in that the cutting edge (15) is situated substantially half-way between two adjacent bars (11).

10. An appliance according to claim 8, characterized in that the cutting edge (15) is situated on one side of the at least one bar (11).

11. An appliance according to claim 8, characterized in that at least one of the jaws (8 or 9) has a fixture (17) to position the sleeve (4) and the hose (2) between the jaws (8, 9).

12. An appliance according to claim 1, characterized in that the cutting edge (15) is situated substantially half-way between two adjacent bars (11).

13. An appliance according to claim 1, characterized in that the cutting edge (15) is situated on one side of the at least one bar (11).

14. An appliance according to claim 1, characterized in that at least one of the jaws (8 or 9) has a fixture (17) to position the sleeve (4) and the hose (2) between the jaws (8, 9).

15. An appliance according to claim 14, characterized in that the at least one bar (11) and the cutting edge (15) are situated on one jaw (8), and that the fixture (17) is situated on the other jaw (9), the at least one bar, the cutting edge and the fixture being mounted on or being made in one piece with the associated jaw.

16. An appliance according to claim 15, characterized in that the jaw (8) provided with the at least one bar (11) and the cutting edge (15) has the form of a die, which is fixedly mounted in the appliance (1), and that the jaw (9) provided with the fixture (17) has the form of a punch, which is movably arranged in the appliance (1) and actuatable by a driving means (10).

17. An appliance according to claim 16, characterized in that it has the form of a pair of tongs (5) which is hand-operated and has one fixed and one movable leg (6, 7), the movable leg (7) actuating the jaw (9) forming the punch by means of a gear device, preferably an eccentric mechanism or the like, forming the driving means (10).

18. An appliance for mechanical sealing of hollow hoses (2) of elastic material with a sealing means (3) which is made of plastically deformable material and which is applied to the hose, said appliance (1) having two jaws (8, 9), both of the jaws are movable towards and away from each other and which, when moving towards each other, crimp the sealing means (3) against the hose (2) to seal the same, characterised in that the sealing means (3) has the form of a sleeve (4) which is slipped on to the hose (2), that at least one of the jaws (8 or 9) has at least one straight bar (11) having a projecting end which projects towards the other jaw (9 or 8) and which, when the jaws (8, 9) are moving towards each other, makes an indentation (12) in the sleeve (4) and the hose (2) to reinforce the sealing thereof as well as the fixing of the sleeve on the hose, that at least one of the jaws (8 or 9) and which, when the jaws (8, 9) are moving towards each other, makes a cutting indication (14) in the sleeve (4) and the hose (2) to allow a sealing cutting of the hose (2), and that the cutting means (13) has the form of a substantially straight cutting edge (15), which projects to a greater extent than the projecting end of said at least one bar (11).

* * * * *